US005649954A

United States Patent [19]
McEwen

[11] Patent Number: 5,649,954
[45] Date of Patent: *Jul. 22, 1997

[54] TOURNIQUET CUFF SYSTEM

[76] Inventor: James A. McEwen, 10551 Bamberton Dr., Richmond, B.C., Canada, V7A 1K6

[ * ] Notice: The term of this patent shall not extend beyond the expiration date of Pat. No. 5,454,831.

[21] Appl. No.: 537,405

[22] Filed: Oct. 2, 1995

Related U.S. Application Data

[63] Continuation-in-part of Ser. No. 194,744, Feb. 9, 1994, Pat. No. 5,454,831, which is a continuation-in-part of Ser. No. 767,812, Sep. 30, 1991, Pat. No. 5,312,431.

[51] Int. Cl.$^6$ ............................................. A61B 17/00
[52] U.S. Cl. ................................. 606/202; 128/672
[58] Field of Search ............................ 606/201–204; 128/672, 677, 685

[56] References Cited

U.S. PATENT DOCUMENTS

| | | | |
|---|---|---|---|
| 2,031,870 | 4/1936 | Vertuno | 128/327 |
| 2,444,161 | 6/1948 | Hanafin | 606/202 |
| 2,943,859 | 5/1960 | Koski et al. | 273/189 A |
| 3,095,873 | 7/1963 | Edmunds | 128/2.05 |

(List continued on next page.)

FOREIGN PATENT DOCUMENTS

| | | |
|---|---|---|
| 0264848 | 4/1988 | European Pat. Off. . |
| 695842 | 12/1930 | France . |
| 2204388 | 5/1974 | France . |
| 0270046 | 8/1935 | Italy . |
| 655385 | 4/1979 | U.S.S.R. . |
| 1193759 | 6/1970 | United Kingdom . |
| 2253789 | 9/1992 | United Kingdom . |
| WO93/06782 | 4/1993 | WIPO . |

OTHER PUBLICATIONS

PCT International Search Report for International Application PCT/IE 96/00065, Sep. 30, 1996.
J.A. McEwen and G.F. Auchinleck, "Advances in Surgical Tourniquets" in JAORN,vol. 36 (1982) pp. 889–896.
J.A. Shaw and D.J. Murray, "The Relationship Between Tourniquet Pressure and . . . " in J. Bone and Joint Surgery, vol. 64A (1982) pp. 1148–1152.
J.A. McEwen and R.W. McGraw, "An Adaptive Tourniquet for Improved Safety in Surgery" in IEEE Trans. Bio–Med Eng., vol. BME 29 (1982) pp. 122–128.
J.A. Shaw et al., "Guidelines for the Use of Digital Tourniquets . . . " in J. Bone & Joint Surgery, vol. 67A (1985) pp. 1086–1090.
A.C. McLaren and C.H. Rorabeck, "The Pressure Distribution Under Tourniquets" in J. Bone and Joint Surg. 67A (1985) pp. 433–438.
R.J. Newman and A. Muirhead, "A Safe and Effective Low Pressure Tourniquet" in J. Bone and Joint Surg., vol. 68B (1986) pp. 625–628.
S.E. Grice et al., "Intravenous Regional Anesthesia: Evaluation and Prevention of Leakage . . . " in Anesthesiology, vol. 65 (1986) pp. 316–320.
M. J. Breault et al., "Internal Pressure Distribution . . . " in Proc. Can. Med. Biol. Eng. Conf. (1989 Toronto) pp. 47–49.

(List continued on next page.)

Primary Examiner—Edgar S. Burr
Assistant Examiner—Anthony H. Nguyen
Attorney, Agent, or Firm—Klarquist Sparkman Campbell Leigh & Whinston, LLP

[57] ABSTRACT

A tourniquet cuff provides a convenient and safe mechanism for connecting a sterile cuff that is disposed within a sterile surgical field with a source of pressurized air outside of the sterile field. Also provided is mechanism for connecting the cuff's inflatable bladder to the end of a tube to establish a gas-tight passageway between the tube and the bladder while allowing rotation of the tube end relative to the bladder in clockwise and counterclockwise directions around the cylindrical axis of the tube and maintaining the gas-tight passageway during and after such rotation and while also ensuring that an operator can disconnect the tube from the bladder only by manually applying an unlocking force and by applying a disconnecting force in a direction at a right angle to the unlocking force while the unlocking force remains applied.

15 Claims, 4 Drawing Sheets

U.S. PATENT DOCUMENTS

| | | | |
|---|---|---|---|
| 3,120,846 | 2/1964 | Fletcher | 606/202 |
| 3,454,010 | 7/1969 | Lilligren et al. | 606/202 |
| 3,467,077 | 9/1969 | Cohen | 606/202 |
| 3,504,675 | 4/1970 | Bishop, Jr. | 606/202 |
| 3,587,584 | 6/1971 | Keller | 128/327 |
| 3,670,735 | 6/1972 | Hazlewood | 128/327 |
| 3,825,008 | 7/1974 | Shook | 606/202 |
| 3,906,937 | 9/1975 | Aronson | 128/205 |
| 4,254,773 | 3/1981 | Waldbillig | 128/348 |
| 4,399,809 | 8/1983 | Bard et al. | 606/202 |
| 4,469,099 | 9/1984 | McEwen | 128/327 |
| 4,479,494 | 10/1984 | McEwen | 128/327 |
| 4,605,010 | 8/1986 | McEwen | 128/686 |
| 4,635,635 | 1/1987 | Robinette-Lehman | 128/327 |
| 4,637,394 | 1/1987 | Racz et al. | 128/327 |
| 4,716,906 | 1/1988 | Ruff | 128/686 |
| 4,770,175 | 9/1988 | McEwen | 128/327 |
| 4,771,790 | 9/1988 | Yamasawa et al. | 128/686 |
| 4,869,265 | 9/1989 | McEwen | 128/774 |
| 4,969,879 | 11/1990 | Lichte | 604/283 |
| 4,979,953 | 12/1990 | Spence | 606/202 |
| 5,048,536 | 9/1991 | McEwen | 128/748 |
| 5,135,473 | 8/1992 | Epler et al. | 606/201 |
| 5,179,941 | 1/1993 | Siemssen et al. | 128/40 |
| 5,254,087 | 10/1993 | McEwen | 604/66 |
| 5,312,431 | 5/1994 | McEwen | 606/202 |
| 5,514,155 | 5/1996 | Daneshvar | 606/201 |

OTHER PUBLICATIONS

J.A. McEwen et al., "Development and Evaluation of . . . " in Proc. 15th Can. Med. Biol. Eng. Conf. (1989 Toronto) pp. 107–108.

PCT International Search Report for International Application PCT/IE 92/00005, Jan. 5, 1993.

"CPC Couplings are Designed for Small Flexible Tubing Applications" (3–page publication) circa Jan. 1991.

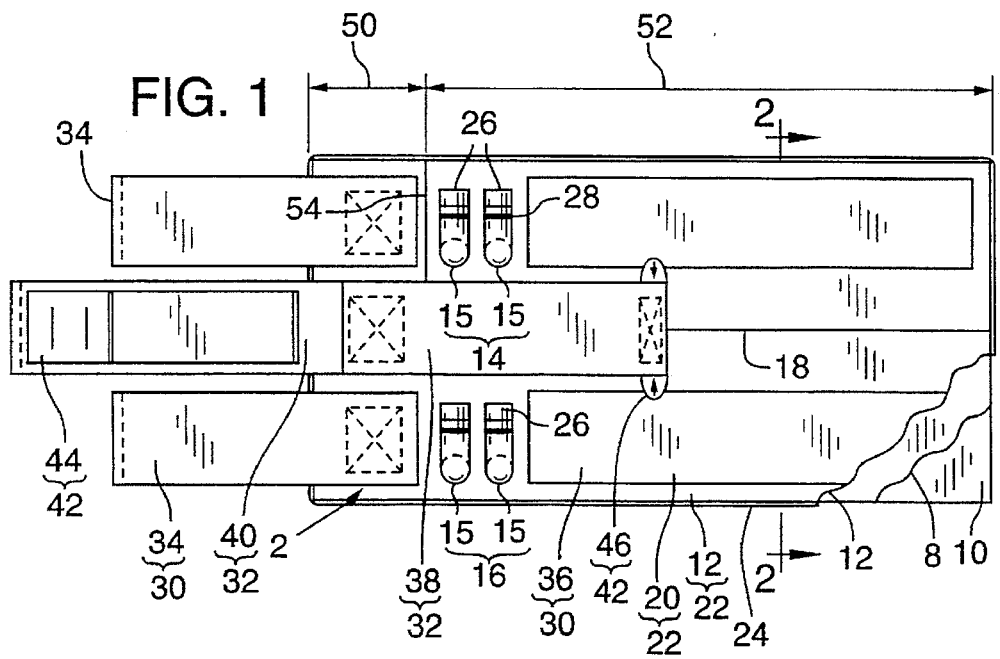
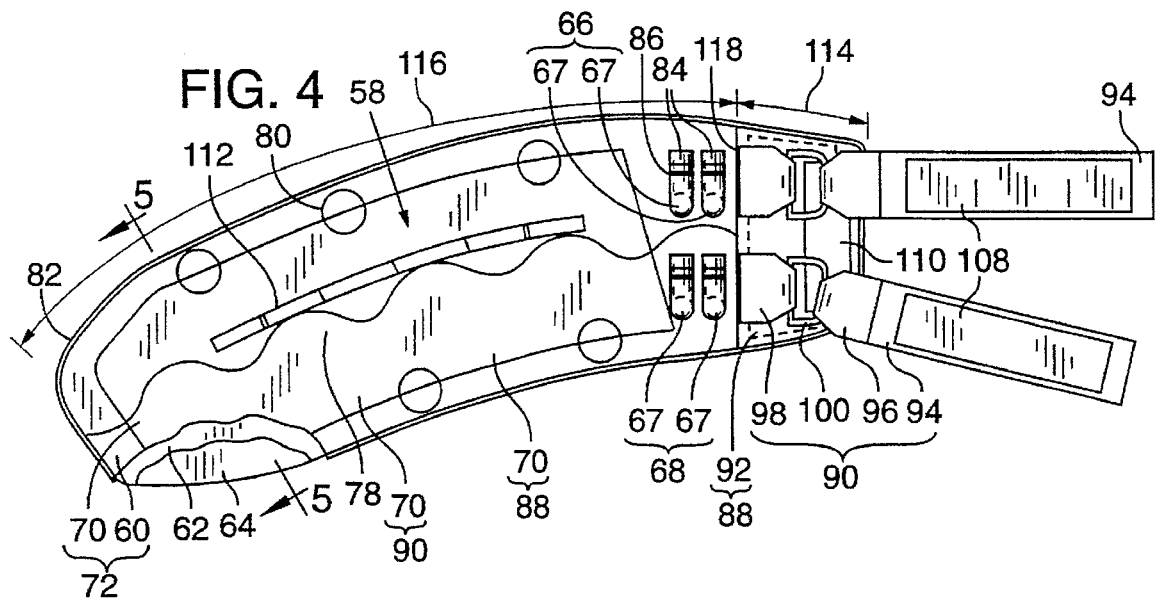

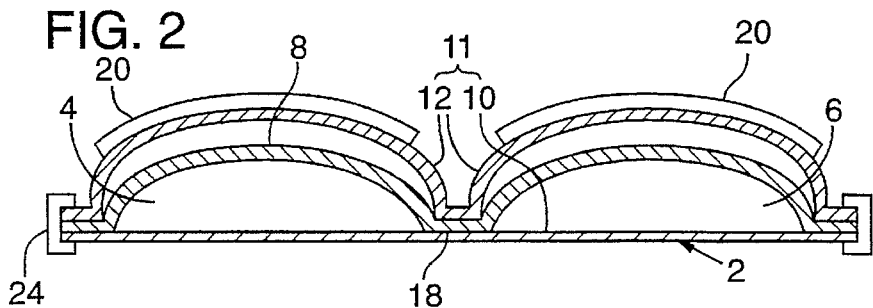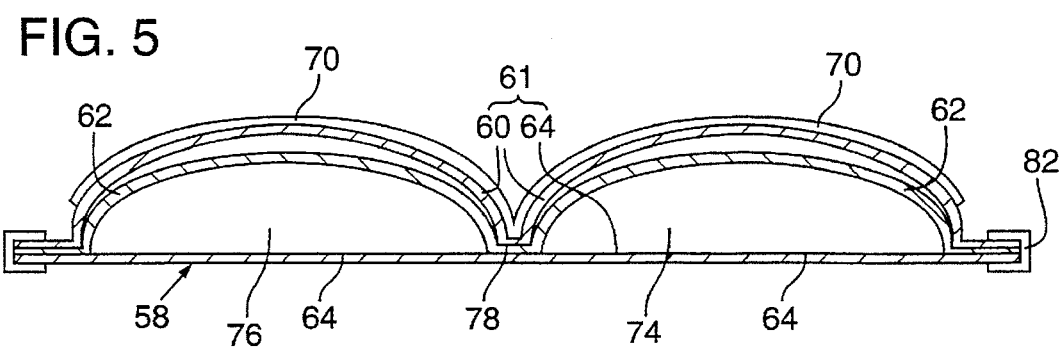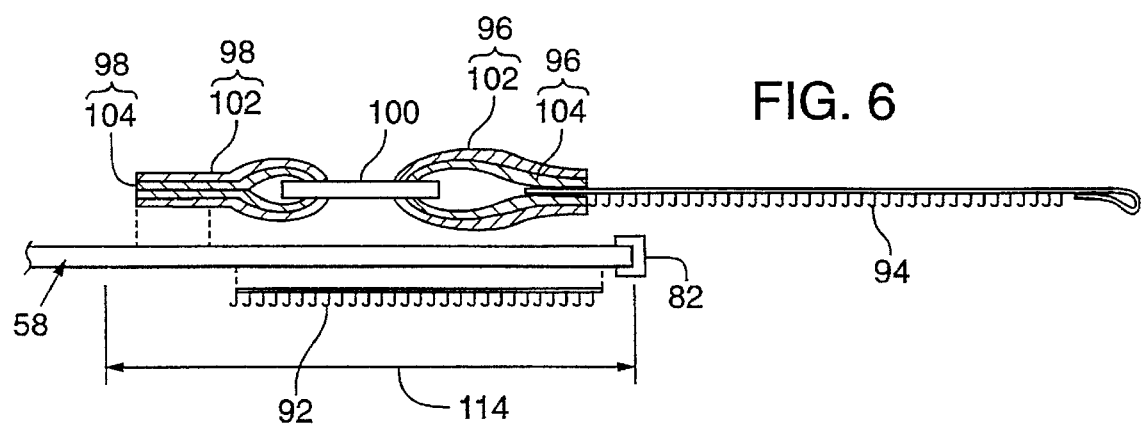

TOURNIQUET CUFF SYSTEM

This is a continuation-in-part of U.S. Patent application Ser. No. 08/194,744 filed Feb. 9, 1994, now U.S. Pat. No. 5,454,831, which was a continuation-in-part of U.S. Patent application Ser. No. 07/767,812, filed Sep. 30, 1991, now U.S. Pat. No. 5,312,431. U.S. Pat. No. 5,454,831, is hereby incorporated by reference.

FIELD OF THE INVENTION

This invention pertains to cuffs for occluding flow in blood vessels in human limbs encircled by the cuffs.

BACKGROUND OF THE INVENTION

The use of an inflatable cuff to occlude blood flow into a subject's limb, thereby providing a bloodless surgical field in the portion of the limb distal to the cuff over a time period suitably long for the performance of a surgical procedure, is well known in surgical practice. When employed to provide a bloodless surgical field, occlusive cuffs constitute one element of a surgical tourniquet system. Tourniquet systems typically include the following basic elements: a source of pressurized gas, an inflatable cuff for encircling a limb at a selected location, and a pressure regulating mechanism for controlling and maintaining the pressure of gas in the inflatable cuff and thus the pressure applied by the cuff to the limb which the cuff encircles. The recent advent of automatic tourniquet systems which employ digital electronic technology in the regulation of pressure and in the detection of certain hazardous conditions has led to significant improvements in the safety and accuracy of surgical procedures performed with an occlusive cuff applied proximally on a limb. These automatic tourniquet systems typically allow the surgeon to safely maintain a constant inflation pressure in the inflatable cuff which he or she estimates to apply pressures to the limb near the minimum required to safely occlude blood flow past the cuff.

Despite improvements in electronic pressure regulation and applied pressure sensing, major limitations exist with respect to safety and efficacy of occlusive cuffs used as part of automatic tourniquet systems. These limitations in prior art occlusive cuffs have persisted despite the increasing use of such cuffs in more demanding surgical procedures, particularly those involving the use of intravenous regional anesthesia (IVRA). In surgical procedures performed under IVRA, the occlusive cuff must be effective in preventing the flow of blood into the field of surgical dissection as well as preventing the premature release of potentially toxic intravenous anesthetics from the veins of the operative limb into the general circulation.

Tourniquet cuffs are often employed in a sterile surgical field. Under such circumstances, it becomes necessary to provide a convenient and reliable mechanism for attaching the cuff to the source of pressurized air (which source is located out of the surgical field) without contaminating the sterile cuff.

Most cuffs of the prior art employ Luer-type connectors to attach the cuffs to tubing connected to the pressure regulators of automated tourniquet systems. These Luer-type connectors have inherent safety limitations, because they have no secondary locking mechanism and they permit easy, inadvertent gas leaks and disconnection as a result of rotation of the tubing with respect to the cuff.

SUMMARY OF THE INVENTION

The invention is directed toward an overlapping occlusive cuff for improved application of pressure to the limb and provides a cuff that includes a convenient and safe mechanism for connecting a sterile cuff that is disposed within a sterile surgical field with a source of pressurized air outside of the sterile field.

The cuff of the present invention also provides: means for connecting the cuff's inflatable bladder to the end of a tube to establish a gas-tight passageway between the tube and the bladder; means to allow rotation of the tube end relative to the bladder in clockwise and counterclockwise directions around the cylindrical axis of the tube; means to maintain the gas-tight passageway during and after such rotation; and means for enabling an operator to disconnect the tube from the bladder only by manually applying an unlocking force and by applying a disconnecting force in a direction at a right angle to the unlocking force while the unlocking force remains applied.

The cuff includes locking connector means for connecting the bladder of the cuff to a tube containing pressurized gas thereby establishing a gas-tight passageway, and having a locking mechanism with release means for locking the bladder and the tube together and maintaining the gas-tight passageway, while allowing bi-directional rotation of the tube with respect to the cuff, until an operator disconnects the bladder from the tube by manually actuating the release means of the locking mechanism while simultaneously pulling the tube away from the cuff.

BRIEF DESCRIPTION OF THE DRAWINGS

A specific embodiment of this invention has been chosen for purposes of illustration and description wherein:

FIG. 1 is a plan view of the specific embodiment of the improved overlapping occlusive cuff for application to a limb substantially cylindrical in shape.

FIG. 2 is a cross-sectional view of the overlapping occlusive cuff of FIG. 1 taken along line A—A'.

An alternate embodiment of this invention has been included for purposes of illustration and description wherein:

FIG. 4 is a plan view of the alternate embodiment of the improved overlapping occlusive cuff for application to a limb substantially conical in shape.

FIG. 5 is a cross-sectional view of the overlapping occlusive cuff of FIG. 4 taken along line B—B'.

FIG. 6 is an exploded view of pivoting secondary safety securing means assembly of the cuff shown in FIG. 4.

Figure 7:
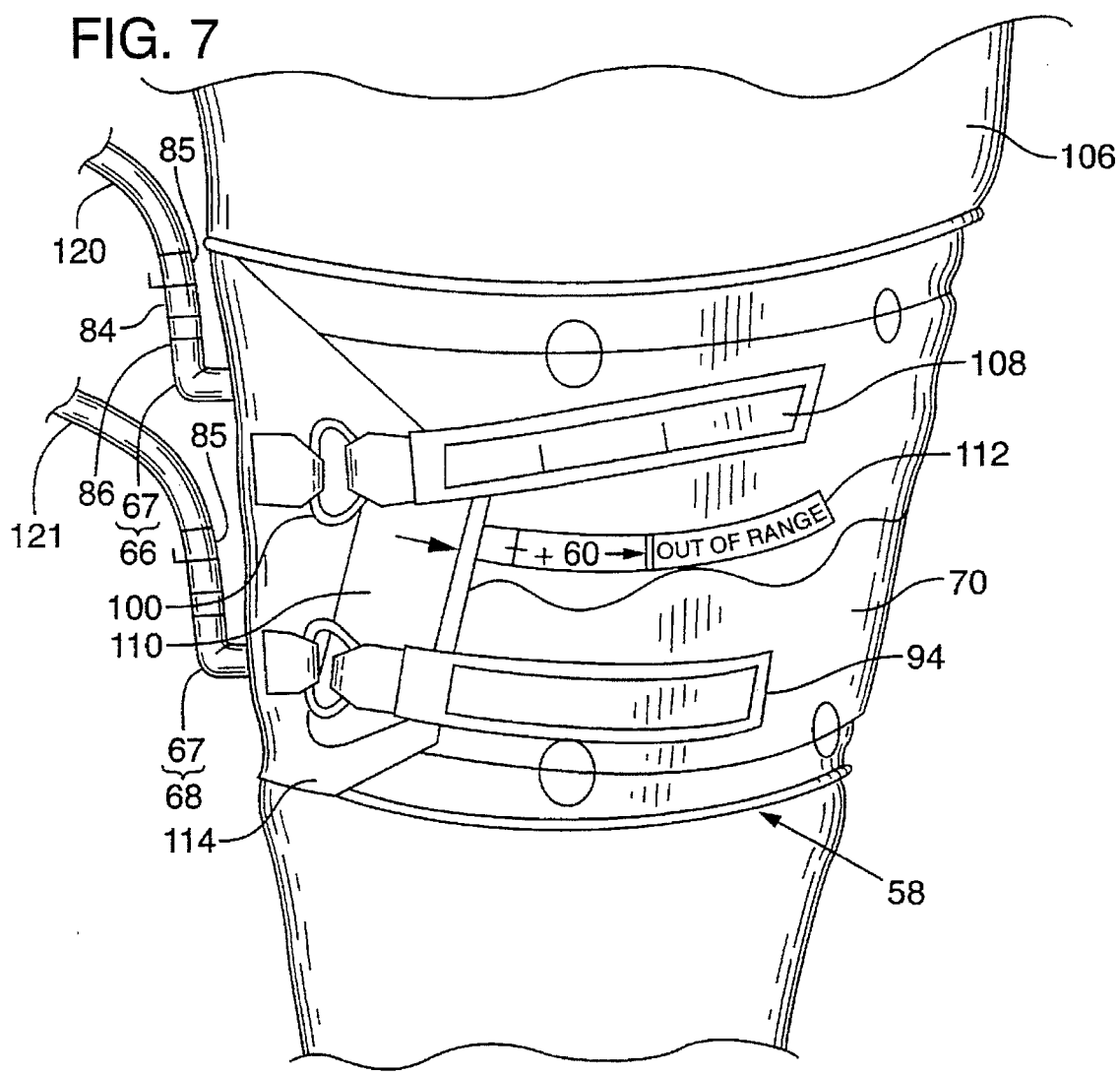

FIG. 7 is pictorial representation of the cuff secondary safety securing means and markings shown in FIG. 4 as applied to a patient's limb.

Figure 8:
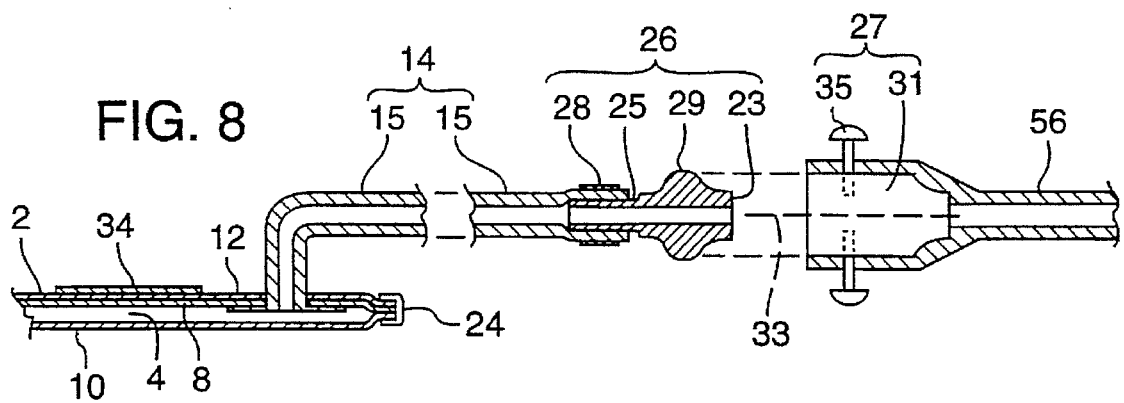

FIG. 8 is a cross-sectional view of the detailed structure of the port of a cuff.

DESCRIPTION OF THE SPECIFIC EMBODIMENT

The specific embodiment illustrated is not intended to be exhaustive or to limit the invention to the precise form disclosed. It is chosen and described in order to explain the principles of the invention and its application and practical use, and thereby enable others skilled in the art to utilize the invention.

FIG. 1 is a plan view illustrating details of an overlapping occlusive cuff 2 having secondary safety securing means for improved safety. Cuff 2 is designed for best shape conformance to limbs substantially cylindrical in shape. Design and fabrication of cuff 2 is similar in certain respects to the design and fabrication of the invention disclosed by Robinette-Lehman in U.S. Pat. No. 4,635,635, but with a number of significant improvements resulting in enhanced safety, efficacy, and cost-effectiveness, as here below described.

Also Robinette-Lehman in U.S. Pat. No. 4,635,635 discloses six cuff sizes whereas, cuff 2 is fabricated in sizes of different length and in a variety of widths to fit 95% of the normal adult size range, so that the surgeon may optimally select cuff 2 by length and width depending on the patient's limb circumference, limb length and the surgical procedure.

As shown in FIG. 1, cuff 2 comprises inflatable bladders 4 and 6 having proximal and distal sides and two ends, wherein the length of the proximal and distal sides is sufficient for the bladder to encircle the limb at a desired location and overlap on itself in a substantially circumferential direction around the limb. Inflatable bladders 4 and 6 are contained in sheath 11 formed by layers 10 and 12, wherein the length of sheath 11 is sufficient for sheath 11 to encircle the limb at a desired location and overlap on itself in a substantially circumferential direction around the limb. Cuff 2 is fabricated using only three layers 8, 10, and 12 and has no internal thermoplastic stiffener. This characteristic results in a cuff design that is thinner and more flexible improving the performance of cuff 2 by providing a more uniform applied pressure to the limb in both the longitudinal axis along the limb as well as at the point where bladders 4 and 6 overlap reducing the number of potential paths for blood flow. This characteristic makes cuff 2 more suitable for pediatric patients with small limb circumferences than other cuffs which are thicker in cross-section. Layers 8, 10, and 12 of cuff 2 are fabricated from a flexible gas-impermeable synthetic cloth, such as a woven nylon backed with a thermoplastic polyurethane coating. This material is substantially inextensible when cuff 2 is pressurized up to 500 mmHg. Layer 12 and bottom layer 10 are coated with polyurethane on one side only and inside layer 8 is coated on both sides. Thermoplastic coatings on layers 8, 10, and 12 facilitate bonding or "heat sealing" in fabrication of cuff 2. The woven nylon surface of layer 10 is a soft, non-wrinkling material. Use of this softer material makes the wider embodiments of cuff 2 more comparable to blood pressure cuffs than other cuffs employing less compliant materials. The materials and fabrication technique of cuff 2 make it economically suitable for limited re-use applications. Other materials for layers 8, 10, and 12 such as flexible thermoplastic polyvinylchloride (PVC)sheeting may be readily substituted for design transferability of cuff 2 to disposable applications in which cuff 2 may be sterile or non-sterile.

Valve sets 14 and 16 include two thermoplastic right-angle ports 15. With respect to valve sets 14 and 16, one port 15 of the set may serve as an opening for cuff inflation and deflation while the other port of the set maybe used for sensing the gas pressure within cuff 2. This feature allows the surgical tourniquet system to detect pressure drops and occluding kinks in the pneumatic tube connecting the tourniquet regulator and cuff 2.

Gas-impermeable inflation bladders 4 and 6 of cuff 2 are formed with bladder dividing heat seal 18 as illustrated in FIG. 2. Inflation bladders 4 and 6 form an integral part of cuff 2 and are not removable. Consequently, in cleaning and inspecting cuff 2 for re-use, errors in re-assembly which can affect safety and performance of cuff 2 have been eliminated.

Inclusion of bladder dividing heat seal 18 results in dual-bladder cuff 2 with bladder 4 permanently isolated from bladder 6. As shown in FIGS. 1 and 2, fluid access to bladder 4 is achieved through port 15 of valve set 14, while fluid access to bladder 6 is through port 15 of valve set 16. In another embodiment of the invention, omission of bladder dividing heat seal 18 results in a single-bladder cuff with one bladder 4. For the single-bladder cuff, fluid access to bladder 4 is achieved by valve set 14 as valve set 16 is omitted.

Referring to FIG. 1, loop material 20 on top layer 12 provides stiffening means in the form of compliant stiffening layer 22 comprised of woven plastic fibers and located above a segment of the overlapped bladders 4, 6 which covers the end of the overlapped bladders 4, 6 that is in closest proximity to the limb, for directing the bladder in the region of the overlap toward the limb when bladders 4, 6 are inflated. Stiffening layer 22 also secures sheath 11 around the limb when bladder 4 or 6 is inflated to a pressure sufficient to stop blood flow in the limb encircled by cuff 2. Layer 22 has a width dimension and a length dimension sufficient for encircling bladders 4 and 6 around the limb. The stiffness of layer 22 can by varied by selecting woven plastic fibers of different thickness and rigidity. The predetermined stiffness of layer 22 directs the portion of the bladder beneath layer 22 toward the limb to produce an applied pressure at predetermined levels near a plurality of predetermined locations on the limb beneath bladders 4 and 6 when bladders 4 and 6 are inflated. This arrangement is chosen to achieve a desired applied pressure gradient so that the risk of injury to nerves underlying cuff 2 is minimized. In addition, substitution of an internal die-cut, integrated thermoplastic stiffener with an external woven fiber stiffener layer 22 that is independent of the inflatable bladders 4 and 6 provides a cuff that is easier to apply and has superior consistency of blood flow occlusion with variations in technique of cuff application. This omission of the internal thermoplastic stiffener significantly reduces the cost to manufacture cuff 2 resulting in a cuff design that is more economical than the majority of tourniquet cuffs of the prior art.

Edge trim 24 consists of a synthetic cloth material such as nylon. Edge trim 24 protects the heat sealed areas of cuff 2 from damage in addition to preventing the rough edges of layers 8, 10, and 12 from contacting the patient.

Figure 3:
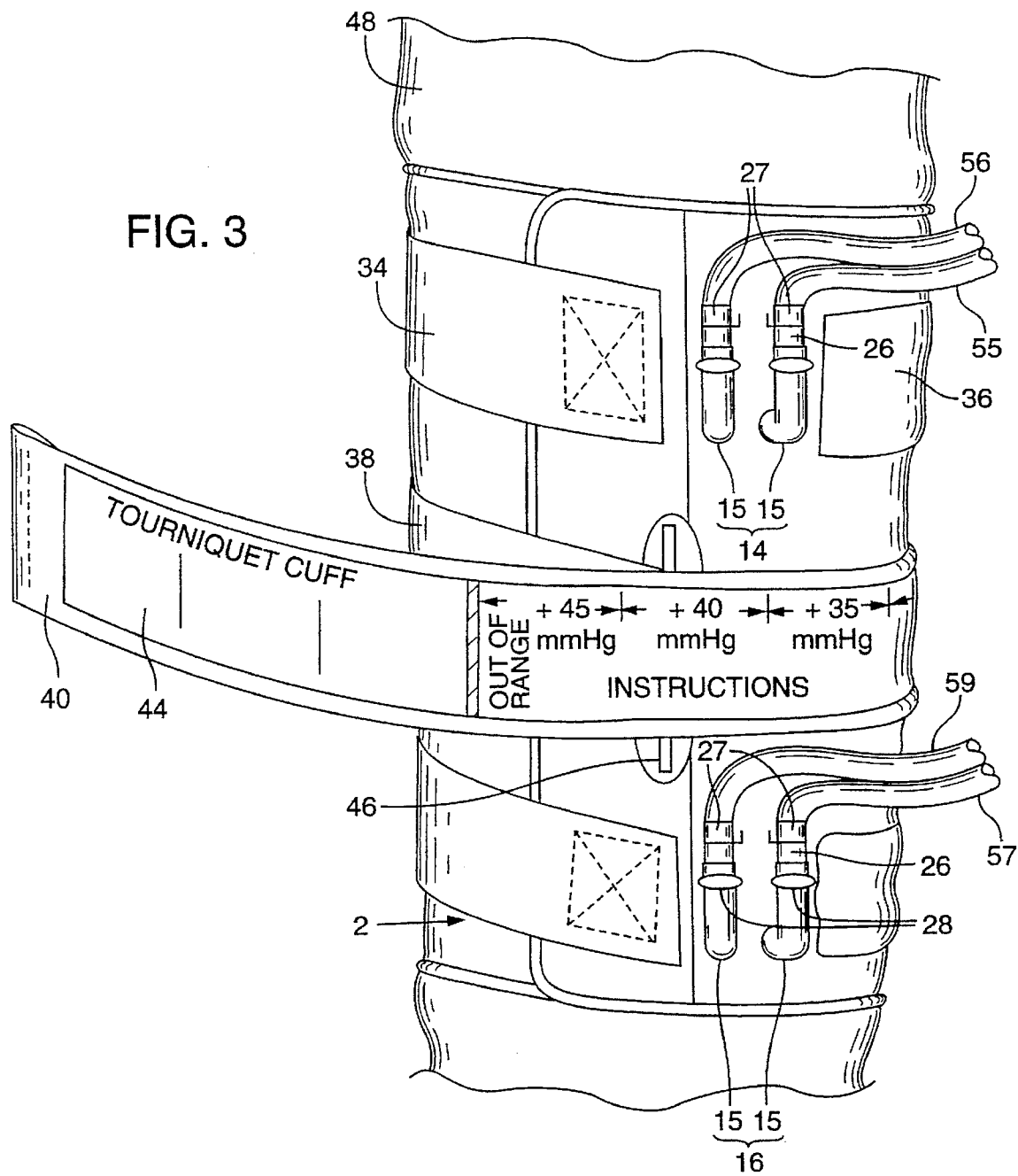
FIG. 3 is a pictorial representation of the overlapping occlusive cuff, secondary safety securing means and markings means shown in FIG. 1 as applied to a patient's limb.

Referring to FIG. 1 and FIG. 3, valve sets 14 and 16 each consist of two right-angle ports 15 attached to bladders 4 and 6, respectively, and provide gas passageways into bladders 4 and 6, respectively, through open ends of the ports. Male pneumatic connectors 26 (PMC 22-04, Colder Products Co, St. Paul Minn.) are inserted into the ports 15 of valve sets 14 and 16, and are non-releasably secured in fixed positions in the ports by self-locking thermoplastic tie straps 28. Matching female pneumatic connectors 27 (PMC 17-02, Colder Products Co, St. Paul Minn.) are inserted into the ends of each of tubes 55, 56, 57 and 59 and are non-releasably attached to or integrally formed with the tubes.

In certain surgical procedures, it is necessary for the cuff 2 to be sterile so that cuff 2 can be located within the sterile surgical field established on limb 48. All of the materials of cuff 2, therefore, are selected from material known to be sterilizable; hence, the properties of these materials are not substantially changed as a result of a sterilization process, which exposes the materials to an electron beam, ethylene oxide gas, gamma radiation or other commonly used sterilizing agents. After sterilization, cuff 2 is free from potentially harmful micro-organisms to a level which satisfies sterility requirements for surgical apparatus used in sterile surgical fields.

When sterile, cuff 2 can be applied around the portion of limb 48 that is within the sterile field; however, sterile cuff 2 must then be connected to tubes 55, 56, 57 and 59 which are not normally sterile. As a result, when cuff 2 is manufactured for use as a sterile cuff, the length of each port is selected to be sufficiently long (for example, greater than the maximum width of cuff 2) so that the outermost end of the port 15 protrudes out of the sterile surgical field. Also, each port 15 is formed of flexible thermoplastic material along at least part of its length, so that each port can be bent for extending past the proximal edge of sterile cuff 2 and out of the sterile surgical field when cuff 2 encircles limb 48 within the sterile surgical field. When all ports extend out of the sterile surgical field, a non-sterile user may join the connector 26 at the end of the port to the non-sterile connector 27 on one of tubes 55, 56, 57 or 59, without contaminating the sterile surgical field.

The embodiment of FIG. 8 shows a port 15, the length of which is extended to facilitate use with a cuff that may be sterilized and used sterile. Referring to FIG. 8, each male pneumatic connector 26 on the ports 15 of valve sets 14 and 16 has a male end 23 which has a cylindrical outside surface about 8 mm in diameter near the end. Around this outside surface, about 8 mm from the end, is annular groove 25, forming a channel about 1 mm wide and 1 mm deep. On the outside surface, closer to end 23 than to the annular groove 25, is a deformable ring 29.

End 23 of the connector 26 fits into a cylindrical receptacle 31 in the female pneumatic connector 27 that is attached to tube 56, so that the axis of the cylindrical receptacle is aligned along the longitudinal axis 33 of the tube at the tube end. A locking metal tab 35 is inserted through the receptacle to engage groove 25 in a direction that is perpendicular to tube axis 33, thus locking and retaining connector 26 and the port of valve set 14 in a constant axial position relative to tube 56 while allowing rotation of the end of the tube 56 around longitudinal axis 33 in both clockwise and counterclockwise directions. When connector 26 is thus received and engaged, the ring 29 of connector 26 is deformed in cylindrical receptacle 31 of connector 27 to establish a gas-tight seal, and this gas-tight seal is maintained during and after rotation of the end of tube 56.

An operator disconnects tube 56 from cuff 2 by applying a non-rotational, unlocking force to locking metal tab 35 in a linear direction that is substantially perpendicular to axis 33 to disengage the locking metal tab 35 from annular groove 25, and by applying a disconnecting force to tube 56 in a linear direction away from the respective connector 26 and along axis 33 of tube 56 at the tube end while the unlocking force remains applied.

Although the male pneumatic connectors 26 of cuff 2 of the specific embodiment are formed from separate components non-releasably attached to the ports 15 of valve sets 14 and 16, alternate means for implementing male pneumatic connectors 26 may be employed. For example, each of the ports 15 of valve sets 14 and 16 may be formed from selected thermoplastic or silicone material having a design which directly incorporates near the port end the substantially cylindrical outside surface of a selected outside diameter, which incorporates directly the annular groove in the outside surface, and which incorporates directly the ring of deformable material on the outside surface of the port end, so that each port can connect directly to one of the connectors 27 attached to tubes 55, 56, 57 and 59. Thus the requirement for attaching a separate pneumatic connector and a separate self-locking thermoplastic tie strap to each of the ports of valve sets 14 and 16 is eliminated, reducing the risk of error in manufacturing cuff 2, increasing the reliability of manufacturing cuff 2, and lowering the cost of manufacturing cuff 2. In the same manner, alternate means for implementing female pneumatic connectors at the ends of tubes 55, 56, 57 and 59 may be employed.

Also, for increased safety, each of the ports of cuff 2 could be further formed directly from selected thermoplastic or silicone material having a different selected shape, length, outside diameter, distance from the port end to the annular groove, or other physical property uniquely matched to the corresponding shape, length, outside diameter, distance to the protruding meatal tab, or other physical property of a connector 27 at the end of a tube, so that a gas-tight connection would not be established between the tube and bladder 4 or 6 of cuff 2 unless the two shapes, lengths, outside diameters, distances or other physical properties corresponded.

The manner in which tubes are connected to cuff 2 of the specific embodiment reduces the risk of accidental disconnection and thus accidental deflation of bladder 4 or 6. Cuffs of the prior art having Luer lock connectors are prone to accidental disconnection due to rotation of the end of the tube connected to such cuffs.

Bladders 4 and 6 are held in place on a limb by bladder securing means 30 and secondary safety securing means 32 which are sufficient to secure bladders 4 and 6 around the limb when either bladder 4 or bladder 6 is inflated to a pressure sufficient to stop blood flow past cuff 2. Secondary safety securing means 32 functions independently of bladder securing means 30 such that bladders 4 and 6 remain overlapped and secured in a substantially circumferential direction if the bladder securing means 30 is not engaged or becomes ineffective while the bladder is inflated to a pressure sufficient to stop arterial blood flow into the limb distal to cuff 2. Bladder securing means 30 consists of hook material 34 and loop material 36. Secondary safety securing means 32, forming a separate and independent securing means from bladder securing means 30, is composed of loop material 38 and hook material 40. Hook material 40 and loop material 38 of secondary safety securing means 32 are different in color from the materials of bladder securing means 30 to distinguish secondary safety securing means 32 and to assist the user in applying cuff 2 to the patient.

Secondary safety securing means 32 also provides independent stiffening means, where each of the overlapping bladders 4 and 6 and the stiffening means overlaps on itself independently around the limb to direct the overlapped bladders 4 and 6 towards the limb and thereby improve application of pressure onto the limb beneath the overlap. This arrangement also allows the snugness of bladders 4 and 6 and snugness of the stiffening means on a limb to be selected independently by an operator. The stiffening means is comprised of woven plastic fibers having preselected stiffness. The selection of material for the stiffening means and the degree of extensibility of the material can be varied to produce applied pressures at predetermined levels near a plurality of predetermined locations on the limb beneath bladders 4 and 6 when bladders 4 and 6 are inflated.

Marking means 42 provides information useful to an operator in determining the pressure to which bladders 4 and 6 should be inflated to occlude blood flow. Marking means 42 comprises one element consisting of a set of graduated markings and another element consisting of a cursor mark whereby the value of a preselected parameter is estimated by the juxtaposition of the cursor mark and one of the set of graduated markings when the secondary safety securing means 32 is secured over the overlapping bladders 4 and 6 in a substantially circumferential direction around the limb. Marking means 42 consists of label 44 sewn to hook material 40 and pointer 46 sewn to the end of loop material 38. Pointer 46 is constructed of semi-rigid thermoplastic sheeting such as polypropylene with a thickness of approximately 1 mm and having a length sufficient to expose a printed arrow or similar indicator when second bladder securing means 32 encircles cuff 2.

FIG. 3 illustrates application of overlapping occlusive cuff 2 to substantially cylindrical limb 48. Label 44 includes markings to restrict use to properly trained staff, instructions detailing proper use of cuff 2 in intravenous regional anesthesia, index markings to identify size range or the maximum and minimum permissible limb circumferences, and a calibrated scale to indicate a recommended minimum inflation pressure for cuff 2 on limb 48. The recommended minimum inflation pressure corresponds to the lowest constant pressure normally required in cuff 2 to safely and reliably occlude blood flow over a time period suitably long for the performance of a surgical procedure when cuff 2 snugly encircles a normal limb of that circumference in a normotensive subject. This information enables the user to safely apply or determine if another tourniquet cuff size would be more appropriate for the patient and to select an inflation pressure for cuff 2 to reduce the risk of underlying nerve injury and achieve improved patient tolerance of cuff 2 when cuff 2 is pressurized.

Fabrication of the overlapping occlusive cuff 2 proceeds through manufacture of a number of subassemblies. First, layers 8, 10, and 12 are die cut from thermoplastic cloth material. At this time, circular openings are die cut into layers 8 and 12 for later passage of valve sets 14 and 16. Loop material 20 is sewn to top layer 12 with loops facing away from layer 12. Valve sets 14 and 16 are inserted through the circular openings previously die cut into layer 8, and flanges of valve sets 14 and 16 are bonded to the bottom coated surface of layer 8 through use of radio frequency heat sealing equipment. Layers 8, 10, and 12 are then manipulated such that valve sets 14 and 16, previously bonded to layer 8, pass through the circular openings in layer 12, and the thermoplastic polyurethane coating of layer 12 contacts the upper coated surface of layer 8 and the thermoplastic polyurethane coating of layer 10 contacts the lower coated surface of layer 8. Following this step, layers 8, 10, and 12 are permanently bonded together at the peripheral edge of cuff 2, at the bladder dividing heat seal 18, and at fluid tight seal 54 through use of the radio frequency heat sealing equipment, thereby forming non-inflatable bladder section 50 and inflatable bladder section 52 contained within sheath 11 formed by layers 10 and 12. This completes the fabrication of the first subassembly.

The second subassembly, or secondary safety securing means 32, is fabricated as follows. Pointer 46 is die cut from polypropylene sheet material which has been previously silk screened with position indicators such as arrows in enamel ink. Label 44, previously silk screened with text in enamel ink, is die cut from nylon sheet material. Loop material 38 is sewn to hook material 40 such that the hooks face away from the loops and material 38 overlaps material 40 by 10 cm. Pointer 46 is then sewn to the end of loop material 38 and label 44 is sewn to the non-hook side of material 40.

In final assembly of cuff 2, edge trim 24 is first sewn around the perimeter of cuff 2 as shown in FIG. 1. Hook material 34 is sewn to the end of section 50 with the hooks facing towards layer 12. Secondary safety securing means 32 is sewn to section 50 such that the hooks of material 40 face layer 12 and the loops of material 38 face away from layer 12. The ends of hook materials 34 and 40 of bladder securing means 30 and 32 are folded over and sewn to provide a small flap for facilitating the release of bladder and secondary safety securing means 30 and 32 upon completion of the surgical procedure. Finally, connectors 26 are inserted into valve sets 14 and 16, and tie straps 28 are wrapped and tightened around valves sets 14 and 16 to secure connectors 26 in place. This completes fabrication of cuff 2.

As shown in FIG. 3, cuff 2 is applied to limb 48 with bladder securing means 30 being fastened followed by secondary safety securing means 32 being wrapped around cuff 2. Hook material 34 engages loop material 20. Adjustment of secondary safety securing means 32, which also functions as an independent stiffening means, allows the user to adjust the snugness of the stiffening means independent of the snugness of overlapped bladders 4 and 6, producing a variable spatial distribution of pressure on encircled limb 48 beneath overlapped bladders 4 and 6 of cuff 2. The user references label 44 to obtain the recommended minimum inflation pressure indicated by the position of pointer 46 with respect to calibrated scale on label 44. Should pointer 46 fall outside the calibrated scale, the user is instructed to select a different size of cuff for the patient. In FIG. 3, cuff 2 is connected by tubes 55, 56, 57 and 59 and connectors 26 to a pressure source providing gas at a regulated pressure between zero and 500 mmHg. This arrangement provides a means of inflating cuff 2 to apply a desired distribution of pressures to limb 48.

DESCRIPTION OF THE ALTERNATE EMBODIMENT

The alternate embodiment illustrated is not intended to be exhaustive or to limit the invention to the precise form disclosed. It is chosen and described in order to explain the principles of the invention and its application and practical use, and thereby enable others skilled in the art to utilize the invention. FIG. 4 is a plan view of the alternate embodiment. FIG. 4 illustrates details of an overlapping occlusive tourniquet cuff 58 having secondary safety securing means for improved safety. Cuff 58 is designed for best shape conformance to limbs substantially conical in shape. As with cuff 2, cuff 58 is fabricated a range of lengths and widths designed to fit 95% of the normal adult size range, so that the surgeon may optimally select cuff 58 by length and width depending on the patient's limb circumference, limb length and the surgical procedure.

Design and fabrication of cuff 58 is similar in certain respects to the design and fabrication of the invention disclosed by Robinette-Lehman in the U.S. Pat. No. 4,635,635 but with a number of significant improvements resulting in enhanced safety, efficacy and cost-effectiveness, as hereinbelow described.

FIG. 4 illustrates an inflatable overlapping occlusive tourniquet cuff 58 for application to limbs substantially conical in shape. Cuff 58 has a substantially arcuate shape with the radius of the arc passing along the width dimension. Cuff 58 has a radial length dimension of 88 cm measured along the centerline of cuff 58 and a width dimension of 20 cm perpendicular to the centerline.

As shown in FIG. 4, cuff 58 comprises inflatable bladders 74 and 76 having proximal and distal sides and two ends, wherein the length of the proximal and distal sides is sufficient for the bladder to encircle the limb at a desired location and overlap on itself in a substantially circumferential direction around the limb. Inflatable bladders 74 and 76 are contained in sheath 61 formed by layers 60 and 64, wherein the length of sheath 61 is sufficient for sheath 61 to encircle the limb at the desired location and overlap on itself in a substantially circumferential direction around the limb. Cuff 58 is fabricated using only three layers 60, 62, and 64 and has no internal thermoplastic stiffener. This characteristic results in a cuff design that is thinner and more flexible improving the performance of cuff 58 by providing a more uniform applied pressure to the limb in both the longitudinal axis along the limb as well as at the point where bladders 74 and 76 overlap reducing the number of potential paths for blood flow. This characteristic makes cuff 58 more suitable for pediatric patients with small limb circumferences than other cuffs which are thicker in cross section. Layers 60, 62, and 64 of cuff 58 are fabricated from a flexible gas-impermeable synthetic cloth such as a woven nylon backed with a thermoplastic polyurethane coating. This material is substantially inextensible when cuff 58 is pressurized up to 500 mmHg. Layer 60 and bottom layer 64 are coated with polyurethane on one side only, and inside layer 62 is coated on both sides. Thermoplastic coatings on layers 60, 62, and 64 facilitate bonding or "heat sealing" in fabrication of cuff 58. The woven nylon surface of layer 64 is a soft, non-wrinkling material. Use of this softer material makes the wider embodiments of cuff 58 more comparable to blood pressure cuffs than other cuffs employing less compliant materials. The materials and fabrication technique of cuff 58 make it economically suitable for limited re-use applications. Other materials for layers 60, 62, and 64 such as flexible thermoplastic polyvinylchloride (PVC) sheeting may be readily substituted for design transferability of cuff 58 to disposable applications in which cuff 58 may be sterile or non-sterile.

Valve sets 66 and 68 consist of two thermoplastic right-angle ports 67. With respect to valve sets 66 and 68, one port 67 of the set may serve as an opening for cuff inflation and deflation while the other port 67 of the set may be used for sensing the gas pressure within cuff 58. This feature allows the surgical tourniquet system to detect pressure drops and occluding kinks in the pneumatic tube connecting the tourniquet regulator and cuff 58.

Gas-impermeable inflation bladders 74 and 76 of cuff 58 are formed with bladder dividing heat seal 78 as illustrated in FIG. 4. Bladder dividing heat seal 78 is an arcuate sinusoidal wave of a predefined frequency and amplitude which runs parallel to the centerline of cuff 58. Inflation bladders 74 and 76 form an integral part of cuff 58 and are not removable. Consequently, in cleaning and inspecting cuff 58 for re-use, errors in re-assembly which can affect safety and performance of cuff 2 have been eliminated.

Inclusion of bladder dividing heat seal 78 results in dual-bladder cuff 58 with bladder 74 permanently isolated from bladder 76. As shown in FIGS. 4 and 5, fluid access to bladder 74 is through port 67 of valve set 66 while fluid access to bladder 76 is through port 67 of valve set 68. In another embodiment of the invention, omission of heat seal 78 results in a single-bladder cuff with one bladder 74. For the single-bladder cuff, fluid access to bladder 74 is achieved by valve set 66 as valve set 68 is omitted.

Referring to FIG. 4, loop material 70 on top layer 60 provides stiffening means in the form of compliant stiffening layer 72 comprised of woven plastic fibers and located above a segment of the overlapped bladders 74 and 76. Stiffening layer 72 which covers the end of the overlapped bladders 74 and 76 that is in closest proximity to the limb directs the bladders in the region of the overlap toward the limb when bladders 74 and 76 are inflated. Stiffening layer 72 also secures sheath 61 around the limb when bladder 74 or 76 is inflated to a pressure sufficient to stop blood flow in the limb encircled by cuff 58. Layer 72 has a width dimension and a length dimension sufficient for encircling bladders 4 and 6 around the limb. The stiffness of layer 22 can by varied by selecting woven plastic fibers of different thickness and rigidity. The predetermined stiffness of layer 72 directs the portion of the bladder beneath layer 72 toward the limb to produce applied pressures at predetermined levels near a plurality of predetermined locations on the limb beneath bladders 74 and 76 when bladders 74 and 76 are inflated. The selection of materials for the stiffening means and the degree of extensibility of the material can be varied to produce a desired applied pressure on the limb. This arrangement is chosen to achieve a desired applied pressure gradient so that the risk of injury to nerves underlying cuff 58 is minimized. In addition, substitution of an internal die cut, integrated thermoplastic stiffener with an external woven fiber stiffener layer 72 that is independent of the inflatable bladders 74 and 76 provides a cuff that is easier to apply and has superior consistency of blood flow occlusion with variations in technique of cuff application. This omission of the internal thermoplastic stiffener significantly reduces the cost to manufacture cuff 58 resulting in a cuff design that is more economical than the majority of tourniquet cuffs of the prior art.

Partial fluting means comprised of a plurality of seams located at preselected distances from the two end edges of the bladders 74 and 76 controls the expansion of bladders 74 and 76 when cuff 58 is inflated. Partial flutes 80 are positioned to overlap both layer 60 and the edge of loop material 70 and are heat sealed to permanently bond layers 60, 62, 64, and 70 together thereby preventing expansion of bladders 74 and 76 within the region of the partial flutes 80. The frequency of the partial flutes 80 on the proximal and distal edges of cuff 58 reduces the tendency of cuff 58 to rolling down the limb when bladders 74 and 76 of cuff 58 are pressurized.

Edge trim 82 consisting of synthetic cloth material such as nylon. Edge trim 82 protects the heat sealed areas of cuff 58 from damage in addition to preventing the rough edges of layers 60, 62, and 64 from contacting the patient.

Referring to FIG. 4 and FIG. 7, valve sets 66 and 68 each include two right-angle ports 67 attached to bladders 74 and 76 respectively which provide gas passageways into bladders 74 and 76 respectively through open ends of the ports. Male pneumatic connectors 84 (PMC 22-04, Colder Products Co, St. Paul Minn.) are inserted into the ports 67 of valve sets 66 and 68, and are non-releasably secured in fixed positions in the ports by self-locking thermoplastic tie straps 86. Matching female pneumatic connectors 85 (PMC 17-02, Colder Products Co, St. Paul Minn.) are inserted into the ends of each of tubes 120 and 121 shown in FIG. 7 and are non-releasably attached in fixed positions. The detailed structure of each port 67 of valve sets 66 and 68 on cuff 58, including attached male pneumatic connector 84, as well as the end of each of tubes 120 and 121 and female pneumatic connector 85, is the same as shown in FIG. 8 for cuff 2, the port 15 of valve set 14, and connectors 26 and 27.

All of the materials of cuff 58 are selected to be sterilizable. The properties of these materials are not substantially changed as a result of a sterilization process which exposes the materials to an electron beam, ethylene oxide gas, gamma radiation or other commonly used sterilizing agents. After sterilization, cuff 58 is free from potentially harmful micro-organisms to a level which satisfies sterility requirements for surgical apparatus used in sterile surgical fields. When sterile, cuff 58 can be applied around the portion of limb 106 that is within the sterile field; however, sterile cuff 58 must then be connected to tubes such as tubes 120 and 121 shown in FIG. 7 which are not normally sterile. As a result, when cuff 58 is manufactured for use as a sterile cuff, the length of each port is selected to be sufficiently long (for example, greater than the maximum width of cuff 58) so that the outermost end of the port 67 protrudes out of the sterile surgical field. Also, each port 67 is formed of flexible thermoplastic material along at least part of its length, so that each port can be bent for extending past the proximal edge of sterile cuff 58 and out of the sterile surgical field when cuff 58 encircles limb 106 within the sterile surgical field. When all ports extend out of the sterile surgical field, a non-sterile user may join the connector 84 at the end of the port to the non-sterile connector 85 a tube such as one of tubes 120 and 121 shown in FIG. 7 without contaminating the sterile surgical field.

Although the male pneumatic connectors 84 of cuff 58 of the alternate embodiment are formed from separate components non-releasably attached to the ports of valve sets 66 and 68, alternate means for implementing male pneumatic connectors 84 may be employed. For example, each of the ports of valve sets 66 and 68 may be formed from selected thermoplastic or silicone material having a design which directly incorporates near the port end the substantially cylindrical outside surface of a selected outside diameter, which incorporates directly the annular groove in the outside surface, and which incorporates directly the ring of deformable material on the outside surface of the port end, so that each port can connect directly to one of connectors 85 and tubes 120 and 121 shown in FIG. 7. Thus the requirement for attaching a separate pneumatic connector and a separate self-locking thermoplastic tie strap to each of the ports of valve sets 66 and 68 is eliminated, reducing the risk of error in manufacturing cuff 58, increasing the reliability of manufacturing cuff 58, and lowering the cost of manufacturing cuff 58. In the same manner, alternate means for implementing female pneumatic connectors at the ends of tubes 120 and 121 shown in FIG. 7 may be employed. Also, for increased safety, each of the ports of cuff 58 could be further formed directly from selected thermoplastic or silicone material having a different selected shape, length, outside diameter, distance from the port end to the annular groove, or other physical property uniquely matched to the corresponding shape, length, outside diameter, distance to the protruding metal tab, or other physical property of a connector 85 at the end of a tube, so that a gas-tight connection would not be established between the tube and bladder 74 or 76 of cuff 58 unless the two shapes, lengths, outside diameters, distances or other physical properties corresponded.

The manner in which tubes are connected to cuff 58 of the alternate embodiment reduces the risk of accidental disconnection and thus accidental deflation of bladder 74 or 76. Cuffs of the prior art having Luer lock connectors are prone to accidental disconnection due to rotation of the end of the tube connected to such cuffs.

Bladders 74 and 76 are held in place on a limb by bladder securing means 88 and secondary safety securing means 90 which are sufficient to secure bladders 74 and 76 around the limb when either bladder 74 or bladder 76 is inflated to a pressure sufficient to stop blood flow past cuff 58. Secondary safety securing means 90 functions independently of bladder securing means 88 such that bladders 74 and 76 remain overlapped and secured in a substantially circumferential direction if the bladder securing means 88 is not engaged or becomes ineffective while the bladder is inflated to a pressure sufficient to stop arterial blood flow into the limb distal to cuff 58.

Bladder securing means 88 consists of hook material 92 and loop material 70 as shown in FIG. 4 and FIG. 6. Secondary safety securing means 90, forming a separate and independent securing means from bladder securing means 88, is composed of loop material 70, hook material 94, attachment loops 96 and 98, and reinforced thermoplastic rings 100. Rings 100 of secondary safety securing means 90 allow hook material 94 to pivot and engage loop material 70 over a range of angles with respect to the centerline of cuff 58. Rings 100 are D-shaped and are injection molded from a plastic resin impregnated with reinforcing agents such as glass or carbon fiber. Loops 96 and 98 of secondary safety securing means 90 consist of layers 102 and 104 are fabricated from a thermoplastic polyurethane coated synthetic cloth similar to the material of layer 60.

FIG. 7 illustrates application of overlapping occlusive cuff 58 to substantially conical limb 106. Markings which include label 108 and inflation and alignment guide 110 include markings to restrict use of cuff 58 to properly trained staff, application instructions for securing cuff 58 around limb 106 and instructions detailing proper use of cuff 58 in intravenous regional anesthesia.

Marking means consisting of inflation and alignment guide 110 and label 112 provide information useful to an operator in determining the pressure to which bladders 74 and 76 should be inflated to occlude blood flow. Marking means comprises one element consisting of a set of graduated markings printed on label 112 and another element consisting of a cursor mark located on inflation and alignment guide 110 whereby the value of a preselected parameter is estimated by the juxtaposition of the cursor mark and one of the set of graduated markings when the secondary safety securing means 90 is secured over the overlapping bladders 74 and 76 in a substantially circumferential direction around the limb. Label 112 attached to loop material 70 also includes index markings to identify size range or the maximum and minimum permissible limb circumferences that cuff 58 can be adjusted to fit, and a calibrated scale to indicate a recommended minimum inflation pressure for cuff 58 when applied to limb 106. The recommended minimum inflation pressure corresponds to the lowest constant pressure normally required in cuff 58 to safely and reliably occlude blood flow over a time period suitably long for the performance of a surgical procedure when cuff 58 snugly encircles a normal limb of that circumference in a normotensive subject. This information enables the user to safely apply or determine if another tourniquet cuff size would be more appropriate for the patient and to select an inflation pressure for cuff 58 to reduce the risk of underlying nerve injury and achieve improved patient tolerance of cuff 58 when cuff 58 is pressurized.

Fabrication of the overlapping occlusive cuff 58 proceeds through manufacture of a number of subassemblies. First, layers 60, 62, and 64 are die cut from thermoplastic cloth material. At this time, circular openings are die cut into layers 60 and 62 for later passage of valve sets 66 and 68.

Label 112, previously silk screened with maximum and minimum permissible limb circumferences and a calibrated scale to indicate a recommended minimum pressure for cuff 58 in enamel ink, is sewn to the loop side of loop material 70. Loop material 70 is sewn to top layer 60 with loops facing away from layer 60. Valve sets 66 and 68 are inserted through the circular openings previously die cut into layer 62, and flanges of valve sets 66 and 68 are bonded to the bottom coated surface of layer 62 through use of radio frequency heat sealing equipment. Layers 60, 62, and 64 are then manipulated such that valve sets 66 and 68 previously bonded to layer 62, pass through the circular openings in layer 60, and the thermoplastic polyurethane coating of layer 60 contacts the upper coated surface of layer 62 and the thermoplastic polyurethane coating of layer 64 contacts the lower coated surface of layer 62. Following this step, layers 60, 62, and 64 are permanently bonded together at the peripheral edge of cuff 58, at the bladder dividing heat seal 78, and at fluid tight seal 118 through use of the radio frequency heat sealing equipment, thereby forming non-inflatable section 114 and inflatable bladder section 116 contained within sheath 61 formed by layers 60 and 64. Partial fluting means 80 bonding layers 60, 62, and 64 together using heat seals of either circular or D shaped configuration having an outside diameter of 1.57 cm and inside diameter of 1.19 cm, are formed through use of the radio frequency heat sealing equipment. This completes the fabrication of the first subassembly.

The second subassembly, or secondary safety securing means 90, is fabricated as follows. Labels 108, previously silk screened with text in enamel ink and die cut from nylon cloth material is sewn to the non-hook side of hook material 94. The ends of hook materials 94 of secondary safety securing means 90 are folded over and sewn to provide a small flap for facilitating the release of secondary safety securing means 90 upon completion of the surgical procedure. Assemblies 96 and 98 of secondary safety securing means 90 shown in FIGS. 4 and 6 are constructed by bonding die cut layers 102 and 104 together when the polyurethane coatings of layers 102 and 104 are in contact. Bonded layers 102 and 104 are then passed through rings 100 to form assembly 96 which is sewn to hook material 94 as shown in FIG. 6. Hook material 94 is sewn to assembly 96 such that hooks of material 94 face towards cuff 58.

In final assembly of overlapping occlusive cuff 58, edge trim 82 is first sewn around the perimeter of cuff 58 as shown in FIG. 4. Hook material 92 of bladder securing means 88 is sewn to non-coated surface of layer 64 in section 114 of cuff 58 with hooks facing away from layer 64 as shown in FIGS. 4 and 6. Inflation and alignment guide 110 is sewn to non-coated surface of layer 60 in section 114 of cuff 58. As shown in FIG. 6, secondary safety securing means assembly 90 forming a separate and independent securing means from bladder securing means 88 is completed by passing bonded layers 102 and 104 through rings 100 to form assembly 98 and sewn to layer 60 located in section 114 of cuff 58 such that hooks of material 94 face towards cuff 58. Finally, connectors 84 are inserted into valve sets 66 and 68, and tie straps 84 are wrapped and tightened around valves sets 66 and 68 to secure connectors 84 in place. This completes fabrication of overlapping occlusive cuff 58.

As shown in FIG. 7, cuff 58 is applied to limb 106 with bladder securing means 88 being fastened followed by secondary safety securing means 90. Bladder securing means 88 is secured around limb 106 by hook material 92 engaging loop material 70. Secondary safety securing means 90 is utilized by pivoting hook material 94 and also engaging loop material 70 such that a maximum contact area is achieved. The arcuate shape of cuff 58 and bladder securing means 88 provides conformance adjustment means for adjusting the shape of cuff 58 over a predefined range of tapers so that cuff 58 remains substantially in contact with limb 106 along the width of cuff 58 and circumference of limb 106. This conformance adjustment means increases resistance of cuff 58 to sudden telescoping down limb 106 due to shape mismatch. Inflation and alignment guide 110 indicates to the user the predefined range of tapers to which cuff 58 can conform by specifying that guide 110 must lie between the proximal and distal edges of cuff 58 when cuff 58 is snugly applied to limb 106. The user references label 112 to obtain the recommended minimum inflation pressure indicated by the position of inflation and alignment guide 110 with respect to calibrated scale of label 112. Should inflation and alignment guide 110 fall outside the calibrated scale on label 112, the user is instructed to select a different size of cuff for the patient. In FIG. 7, cuff 58 is connected by tubes 120 and 121 and male pneumatic connectors 84 to a pressure source providing gas at a regulated pressure between zero and 500 mmHg. This arrangement provides a means of inflating cuff 58 to apply a desired distribution of pressures to limb 106.

It is to be understood that the invention is not to be limited to the details herein given but may be modified within the scope of the appended claims.

I claim:

1. A sterile occlusive cuff for facilitating surgery by occluding flow in blood vessels in a patient's limb, comprising:

a sheath having a inflatable portion longer than the circumference of a limb at a desired location on the limb, a width, and a length that is greater than the length of the inflatable portion, the sheath also including a sterile inner side, a sterile outer side, sterile side edges and sterile end edges;

sheath securing means having a sterile first securing element attached to the outer side of the sheath and a sterile second securing element attached to the outer side and extending past an end edge to engage the first securing element when the sheath is applied around a patient's limb, thereby overlapping and securing the inflatable portion of the sheath around the limb;

a port having a first end non-releasably attached to the inflatable portion of the sheath at a location on the sheath, a second end, and a port length between the first end and the second end, wherein the port is comprised of sterile material and includes an annular groove in the outside surface of the port near the second end and a ring of sterile and deformable material extending around the outside surface of the port near the second end, and wherein the port length is such that the second end of the port is extendable past a side edge of the sheath, the port thereby establishing a gas passageway from the second end of the port across the side edge of the sheath and to the inflatable portion of the sheath.

2. The cuff as described in claim 1 and including:

a non-sterile tube having an end and a longitudinal axis at the tube end; and non-sterile tube release means at the tube end including:
  means for receiving the second end of the port;
  means for deforming the deformable material to establish a gas-tight seal when the second end of the port is received;
  locking means engaging the annular groove of the received second end of the port to allow rotation of the tube end while maintaining the second end of the port in a constant axial position relative to the longitudinal axis of the tube;
  and unlocking means for disengaging the locking means from the annular groove in response to the application of a force to the tube release means at approximately a right angle to the longitudinal axis.

3. The cuff as described in claim 2 wherein the non-sterile tube has a second end, and including pressure regulator means adapted to communicate pneumatically with the second end of the tube to supply gas through the tube and port to the inflatable portion of the sheath at a pressure sufficient to occlude flow in blood vessels in the limb encircled by the sheath.

4. The cuff of claim 1 and including a second port having a proximal end non-releasably attached to the inflatable portion of the sheath at a second location on the sheath, a distal end, and a second port length between the proximal end and the distal end, wherein the second port is comprised of sterile material and includes an annular groove in the outside surface of the second port near the distal end and a ring of sterile and deformable material extending around the outside surface of the second port near the distal end, and wherein the second port length is such that the distal end of the second port is extendable past a side edge of the sheath, the port thereby establishing a second gas passageway from the distal end of the port across the side edge of the sheath and to the inflatable portion of the sheath.

5. An improved occlusive cuff for facilitating surgery by occluding flow in blood vessels in a patient's limb, comprising:
 a sheath having an inflatable portion longer than the circumference of a limb at a desired location, a width, a length greater than the length of the inflatable portion, an inner side facing the limb, an outer side facing away from the limb, side edges, end edges, and a port having a first port end, a second port end, a port length and formed of flexible thermoplastic material along a portion of the port length, wherein the first port end is non-releasably attached to the inflatable portion of the sheath at a location and in an orientation such that the second port end may be positioned to reside past a side edge of the sheath, thereby establishing a gas passageway between the inflatable portion of the sheath and the second port end, which passageway extends across the side edge;
 sheath securing means having a first securing element attached to the outer side of the sheath and a second securing element attached to the outer side and extending past an end edge to engage the first securing element when the sheath is applied around the limb at the desired location, thereby overlapping and securing the inflatable portion of the sheath in a substantially circumferential direction around the limb; and
 a tube having an end and a longitudinal axis at the end and connectable at the second end to the port to establish the substantially gas-tight passageway between the inflatable portion of the sheath and the tube through the port;
 wherein the tube end includes manually operable tube release means whereby the tube is disconnectable from the port by the application of an unlocking force to the tube release means in a direction substantially at a right angle to the longitudinal axis of the tube end and by the application of a disconnecting force to the tube end in a direction along the longitudinal axis of the tube end and away from the port while the unlocking force remains applied.

6. The cuff as described in claim 5 wherein the tube has a second end, and including pressure regulator means adapted to communicate pneumatically with the second end of the tube to supply gas through the tube and port to the inflatable portion of the sheath at a pressure sufficient to occlude flow in blood vessels in the limb encircled by the sheath.

7. The cuff of claim 5 and including a second port having a proximal port end, a distal port end, a second port length and formed of flexible thermoplastic material along a portion of the second port length, wherein the proximal port end is non-releasably attached to the inflatable portion of the sheath at a second location and in an orientation such that the second port end may be positioned to reside past a side edge of the sheath, thereby establishing a second gas passageway between the inflatable portion of the sheath and the distal port end residing past the side edge.

8. A cuff as described in claim 5 wherein the sheath and sheath securing means are sterile and wherein the tube is not sterile.

9. A cuff as described in claim 8 wherein the port includes rotational means for allowing rotation of the tube end relative to the connected port in both clockwise and counterclockwise directions around the longitudinal axis of the tube end, and wherein the port includes sealing means for maintaining the substantially gas-tight passageway during and after rotation.

10. A cuff as described in claim 9 wherein the port has an outside surface of substantially cylindrical shape near the second end of the port, wherein the rotational means is an annular groove in the outside surface at a first predetermined distance from the second end of the port, wherein the sealing means is a ring of sterile and deformable material extending around the outside surface at a second predetermined distance from the second end of the port; and
 wherein the manually operable tube release means includes:
  locking means for engaging the annular groove to allow rotation while maintaining the second end of the port end in a constant axial position relative to the longitudinal axis of the tube end; and
  unlocking means for disengaging the locking means from the groove in response to the application of the releasing force.

11. An improved occlusive cuff for facilitating surgery by occluding flow in blood vessels in a patient's limb, comprising:
 a sheath having an inflatable portion longer than the circumference of a limb at a desired location, a width dimension, a length dimension greater than the length of the inflatable portion, an inner side facing the limb, an outer side facing away from the limb, side edges and end edges;
 sheath securing means having a first securing element attached to the outer side of the sheath and a second securing element attached to the outer side and extending past an end edge to engage the first securing element when the sheath is applied around the limb at the desired location, thereby overlapping and securing the inflatable portion of the sheath in a substantially circumferential direction around the limb; and
 a port having a first end, a second end, a predetermined length between the first and second ends, an outer surface of a substantially cylindrical shape near the second end, an annular groove in the outer surface at a first predetermined distance from the second end, and a ring of deformable material extending around the outer surface at a second predetermined distance from the second end, wherein the first end of the port is non-releasably attached to the inflatable portion of the sheath at a location and in an orientation such that the port may be extended across a side edge of the sheath, thereby establishing a gas passageway between the inflatable portion of the sheath and the second end of the port such that the passageway extends past the side edge of the sheath.

12. A cuff as described in claim 11 wherein the sheath, sheath securing means and port are sterile.

13. A cuff as described in claim 12 and including a tube having an end, a longitudinal axis at the tube end; and tube connection means at the tube end including:
   means for receiving the second end of the port;
   means for deforming the deformable material to establish a gas-tight seal when the second end is received;
   locking means engaging the annular groove of the received second end to allow rotation of the second end while maintaining the second end in a constant axial position relative to the longitudinal axis; and
   unlocking means for disengaging the locking means from the annular groove in response to the application of a force to the tube release means in a direction substantially at a right angle to the longitudinal axis.

14. The cuff as described in claim 11 and including pressure regulator means adapted to communicate pneumatically with the port to supply gas through the port to the inflatable portion of the sheath at a pressure sufficient to occlude flow in blood vessels in the limb encircled by the sheath.

15. The cuff of claim 11 and including a second port having a proximal end, a distal end, a predetermined length between the proximal and distal ends, an outer surface of a substantially cylindrical shape near the distal end, an annular groove in the outer surface at a first predetermined distance from the distal end, and a ring of deformable material extending around the outer surface at a second predetermined distance from the distal end, wherein the proximal end of the second port is non-releasably attached to the inflatable portion of the sheath at a second location and in an orientation such that the second port may be extended across a side edge of the sheath, thereby establishing a second gas passageway between the inflatable portion of the sheath and the distal end of the second port that extends across the side edge of the sheath.

\* \* \* \* \*